Figure 1:
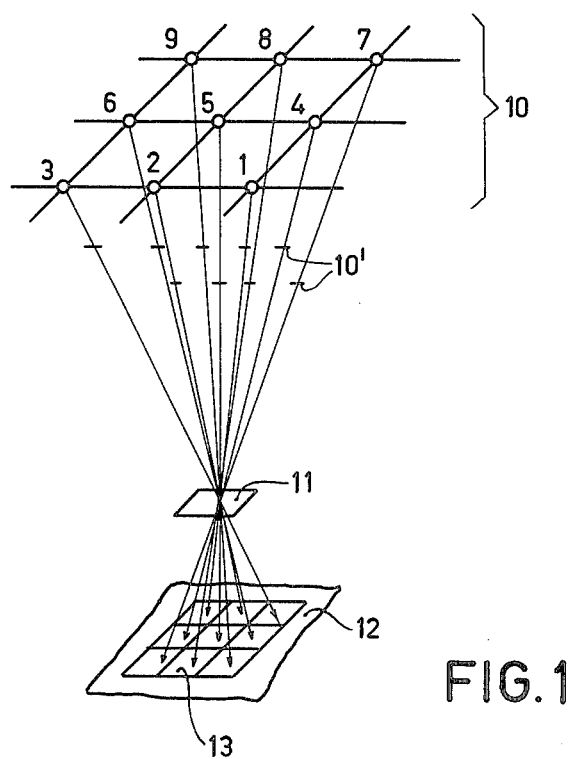

United States Patent [19]

Weiss et al.

[11] 4,246,483
[45] Jan. 20, 1981

[54] X-RAY APPARATUS FOR TOMOSYNTHESIS

[75] Inventors: Hermann Weiss, Hamburg; Rolf Linde, Haseldorf; Ulf Tiemens, Prisdorf; Erhard Klotz, Halstenbek, all of Fed. Rep. of Germany

[73] Assignee: U.S. Philips Corporation, New York, N.Y.

[21] Appl. No.: 3,687

[22] Filed: Jan. 15, 1979

[30] Foreign Application Priority Data
Jan. 13, 1978 [DE] Fed. Rep. of Germany ....... 2801329
Jan. 18, 1978 [DE] Fed. Rep. of Germany ....... 2801940

[51] Int. Cl.³ .......................... A61B 6/00; G03B 41/16
[52] U.S. Cl. ................................. 250/445 T; 250/520
[58] Field of Search ............................ 250/445 T, 520

[56] References Cited
U.S. PATENT DOCUMENTS
4,132,896  1/1979  Klotz ................................. 250/445 T
FOREIGN PATENT DOCUMENTS
1541671  9/1968  France ................................. 250/445 T Primary Examiner—Alfred E. Smith
Assistant Examiner—T. N. Grigsby
Attorney, Agent, or Firm—T. A. Briody; R. T. Mayer; J. E. Haken

[57] ABSTRACT

Apparatus for examining objects includes a group of X-ray sources, which are activated group-wise by a generator. A group of sub-images are separately projected onto a photographic film. During a subsequent step, the film is re-imaged with the aid of an optical lens matrix the lenses in the matrix are arranged in a manner similar to the X-ray sources.

4 Claims, 10 Drawing Figures

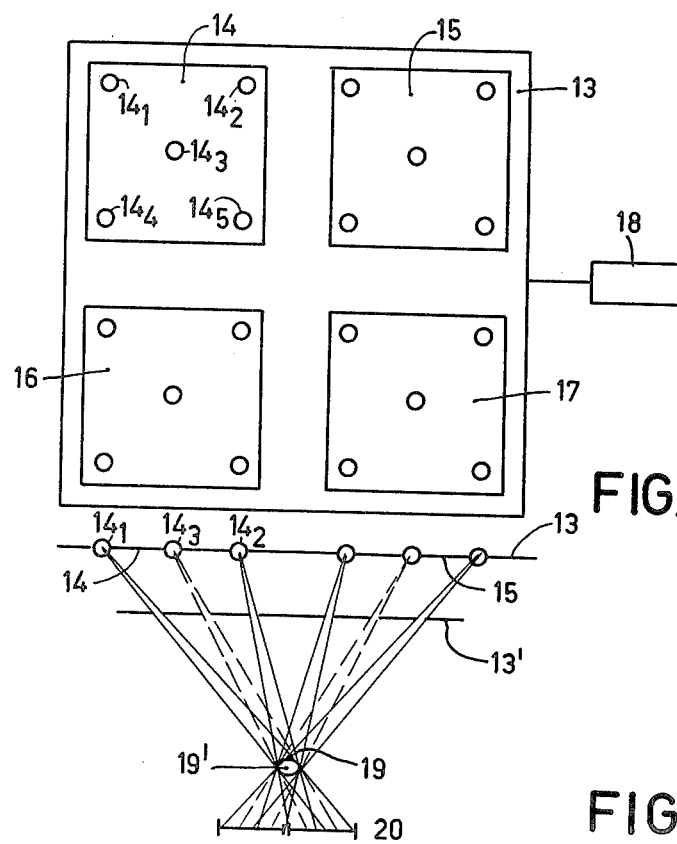
FIG.3a
FIG.3b
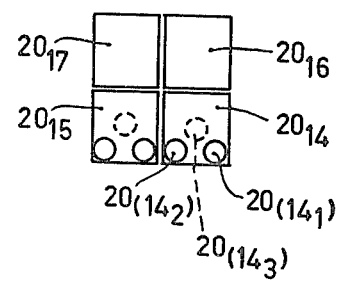
FIG.3c

X-RAY APPARATUS FOR TOMOSYNTHESIS

The invention relates to an apparatus for examining objects, comprising a multiplicity of X-ray sources each having a comparatively small X-ray focus, a generator with a control unit for activating the X-ray sources, and a housing for a flat X-ray registration medium.

Apparatus of this kind is known from German Patent Application No. 2,605,497 which describes apparatus for generating images of layers of three-dimensional objects, especially for medical diagnostics. Annoying artifacts can occur in the image formed by this apparatus due to the geometrical orientation of sub-images on the registration medium.

The invention has for its object to avoid the occurrence of these artifacts, without increasing the complexity of the apparatus. To this end, an apparatus in accordance with the invention is characterized in that the X-ray sources are fixed in a housing in a geometrical arrangement such that a group of mutually separate sub-images can be formed on the registration medium; the X-ray foci being located in a single plane. The X-ray sources are arranged and activated so that mutually separate sub-images are formed on a registration medium with given dimensions in a geometrical arrangement; Thus, a layer of the object is imaged after superposition of the sub-imaged for the image reconstruction with a minimum of image deterioration from other layers. This kind of imaging is described in Optics Communications, Vol. 11, No. 4 (1974), page 368, Optical Cummunications Vol. 12, No. 2 (1974), page 183 and IEEE C-24 (1977), page 391.

In a preferred embodiment of the apparatus in accordance with the invention, the X-ray sources are formed by fixed anode X-ray tubes which are controlled by a generator provided with the transformer, preferably enclosed in the tube housing, for generating high frequency control pulses.

In another preferred embodiment of the apparatus in accordance with the invention, the exit windows for the X-ray sources are formed by an adjustable aperture mechanism.

Embodiments of the apparatus in accordance with the invention will be described in detail hereinafter with reference to the accompanying diagrammatic drawing.

Figure 2:
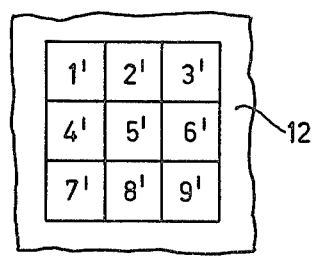
Figure 4:
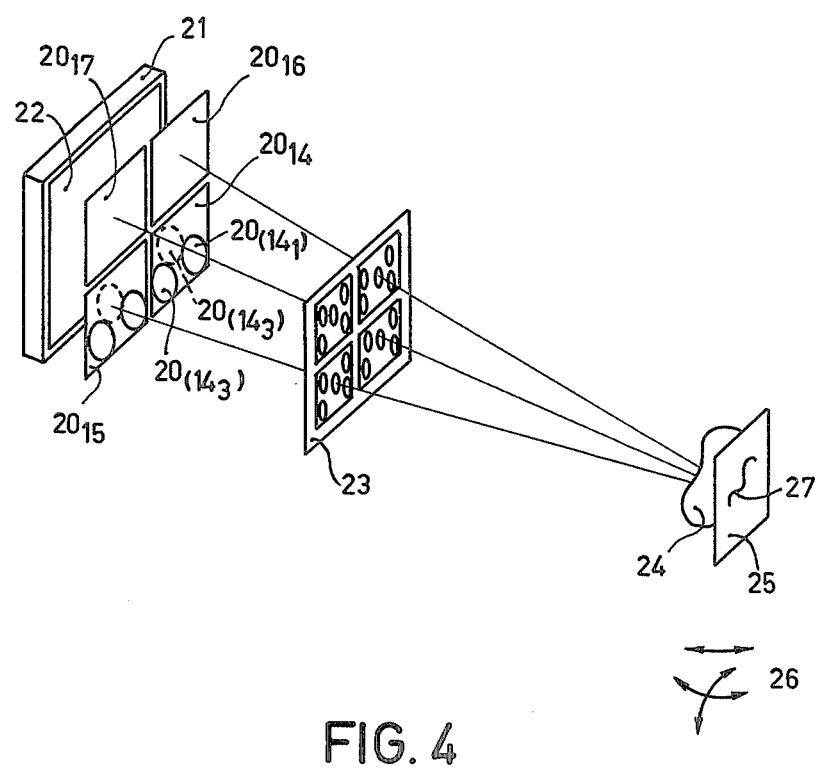
Figure 5:
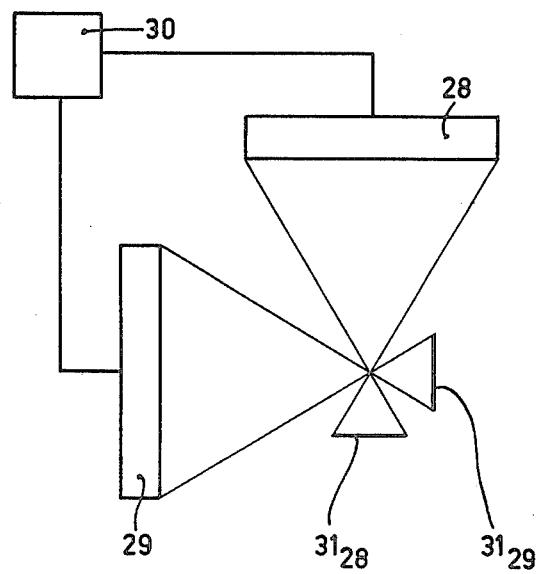
Figure 6:
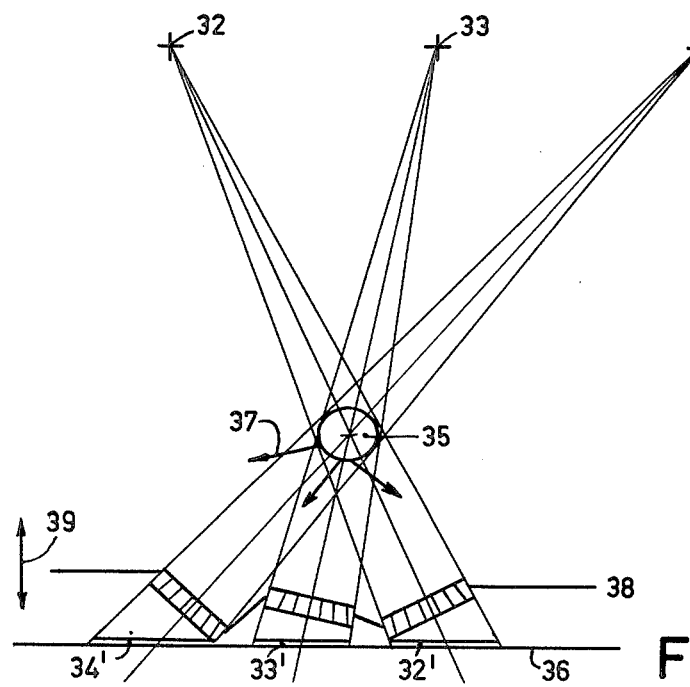
Figure 7:
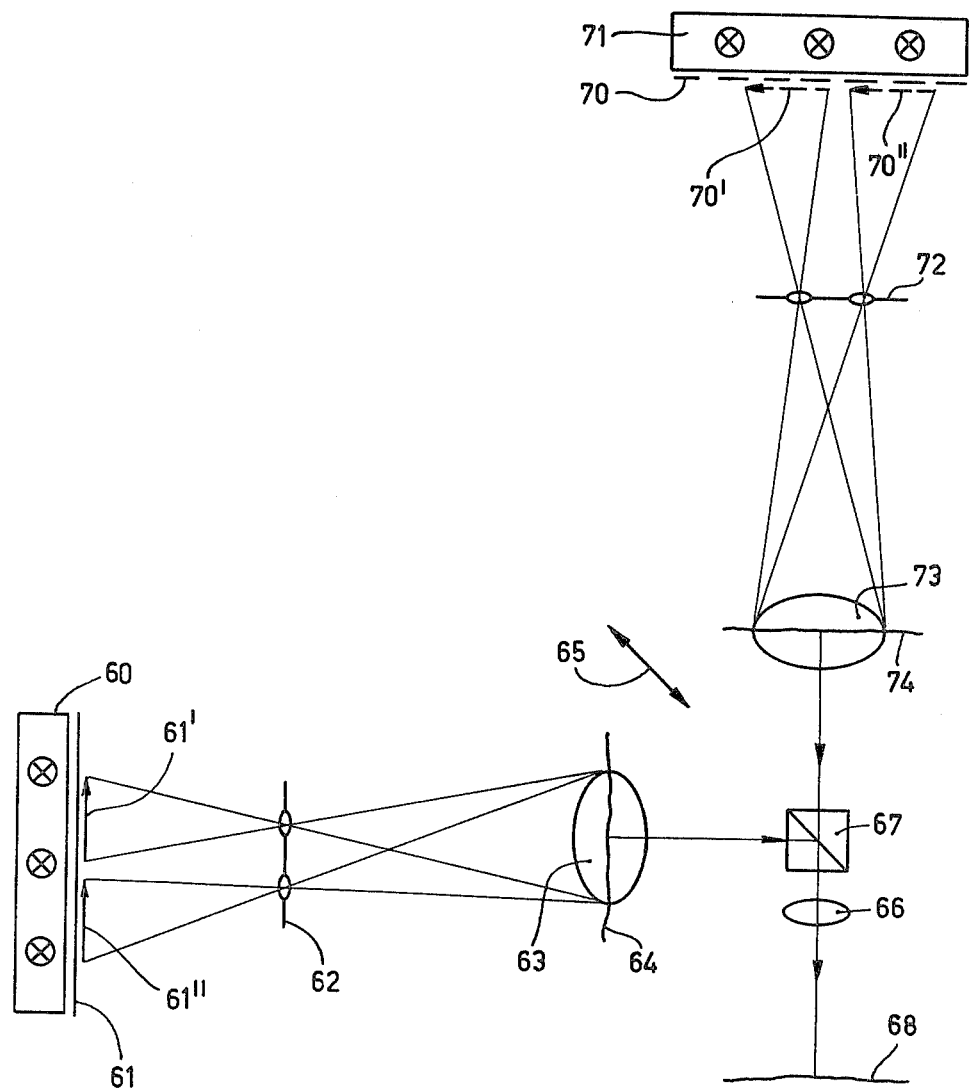

FIG. 1 shows the principle of registering separate sub-images by means of a multiple radiation source, FIG. 2 shows detailed sub-images produced by the arrangement shown in FIG. 1, FIG. 3a shows a multiple radiation source subdivided into four groups, FIG. 3b shows the registration geometry for registering separate sub-images, FIG. 3c shows a checkerboard pattern of four sheet films for registering the sub-images, FIG. 4 shows an example of the formation of the layer image, FIG. 5 shows an arrangement of multiple radiation sources which can be simultaneously activated with groups shifted 90° with respect to each other, FIG. 6 shows a scattered radiation grating arrangement for a multiple radiation source, and FIG. 7 shows an example of optical layer imaging by means of two separate multi-perspective images.

Figure 8:
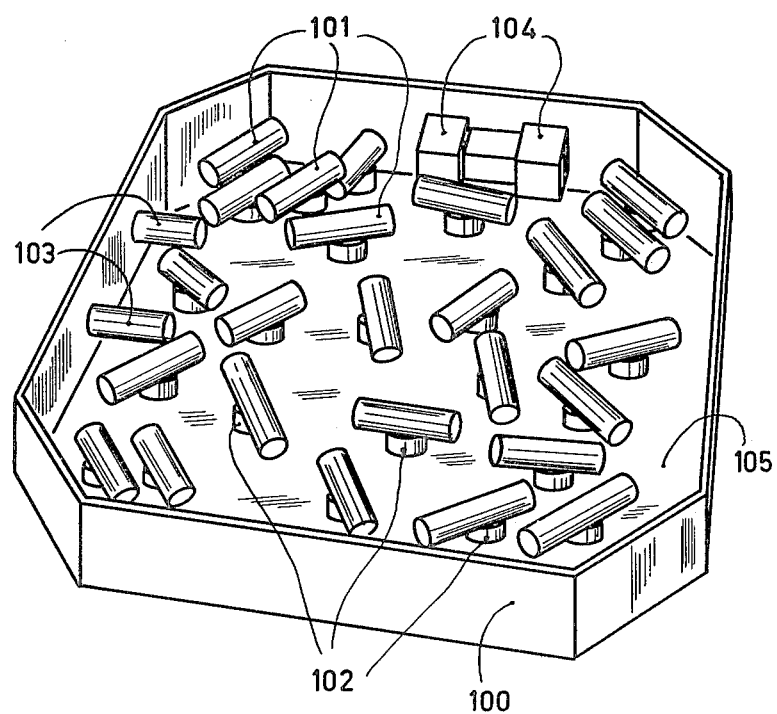

FIG. 8 is a diagrammatic representation of a housing for the X-ray tubes.

In FIG. 1, an object 11 is irradiated by a multiple radiation source arrangement 10, which includes radiation sources 1-9 (for example, X-ray tubes) and mechanical apertures 10'. Sub-image 13 are separately registered on a registration medium 12 (for example, film).

FIG. 2 shows the separate sub-images 1' to 9' on the registration medium 12 of FIG. 1.

FIG. 3a shows a multiple radiation source arrangement 13 consisting of four groups 14, 15, 16 and 17. Each group comprises, for example, five individual tubes (for example, tubes $14_1$, $14_2$, $14_3$, $14_4$, and $14_5$. The complete arrangement 13 can be simultaneously switched by means of a control unit 18.

The X-ray tubes may be accommodated in a common tank for insulation and cooling. Alternatively, only the X-ray tubes in one group can be accommodated in a common tank; it is also possible for each tube to have its own tank. Furthermore, each X-ray tube may have its own high voltage generator. An electric control unit can be provided for all X-ray tubes. The focal points of the individual tubes are centred and oriented in the direction of the object to be imaged. The X-ray tubes can alternatively be controlled by a mechanical aperture device. The beams of the individual tubes are stopped by aperture devices for forming the separate sub-images. So that arbitrary object dimensions can be formed for optimum X-ray film use.

FIG. 3b shows the registration geometry for registering sub-images which are separated into the various groups. For the sake of clarity, only a one-dimensional description of the arrangement is given. The individual tubes $14_1$, $14_2$ and $14_3$ in groups 14 and 15 of the multiple radiation source arrangement 13 are directed onto an object 19. The position and dimensions of an interior layer of the object 19' is indicated by a optical means light visor. The group of sub-images formed are separately registered in a registration plane 20. The radiation beam is stopped by means of an aperture arrangement 13'. Exposure control can, in principle also be performed by this aperture.

FIG. 3c is a detailed representation of the registration plane 20. For example, four sheet films are arranged in a checkerboard pattern; separate sub-images of a group are registered ($20_{14}$, $20_{15}$, $20_{16}$ and $20_{17}$) on each of these films. The group $20_{14}$ comprises, for example, separate sub-images $20(14_1)$ $20(14_2)$ and $20(14_3)$. Corresponding sub-images are formed in the registration plane $20_{15}$.

FIG. 4 shows an arrangement for layer imaging. A light box 21, comprising a frosted glass plane 22, illuminates the four films $20_{14}$, $20_{15}$, $20_{16}$ and $20_{17}$ with each group of separate sub-images, (FIG. 3c). A lens matrix 23, in which the geometrical arrangement of the individual lenses corresponds to the positions of the radiation sources (13 of FIG. 2a), produces a three-dimensional image 24 of the object 19 of FIG. 3b. Each individual lens images the sub-image associated with this position. The layer of interest 27 is imaged on a frosted plane 25 which can be arbitrarily moved within the object image 26.

FIG. 5 shows two multiple radiation source arrangements 28 and 29 which are shifted 90° with respect to each other and which can be simultaneously activated by the control unit 30. The sub-images are registered in registration planes $31_{28}$ and $31_{29}$.

The multiple radiation source arrangements 13 (FIG. 3a) and 28 and 29 (FIG. 5) are of course also suitable for registering coded superposition images. These images are decoded in accordance with the principle shown in FIG. 4.

FIG. 6 shows a scattered radiation grating arrangement for a multiple radiation source arrangement consisting of the tubes 32, 33 and 34. The tubes are directed onto the object 35 and produce the separate sub-images 32', 33' and 34' in the plane of registration 36. The scattered radiation 37 of the object 35 is suppressed by means of the scattered radiation grating 32", 33" which is aligned and focussed, if necessary, with respect to the radiation source. The individual scattered radiation gratings are interconnected (38) and can be moved during the exposure with respect to the plane of registration (36) in order to erase the grating structure. The scattered radiation grating arrangement can also be chosen so that the gratings whose laminations are linearly arranged and directed towards the radiation source are all situated in one and the same plane.

FIG. 7 shows an optical decoding construction for layer imaging. A multi-perspective image 61, comprising sub-images 61' to 61", is illuminated by means of a light box 60. A lens matrix 62, the arrangement of the lenses in which corresponds to the geometrical positions of a first group of multiple radiation source, produces a three-dimensional object image 63. Arbitrary layers can be imaged using a frosted plane 64 which can be shifted within the object image by means of a shifting device 65. An objective 66 projects the image from the frosted plane 64, via a beam splitter 67, onto a further frosted screen 68. A second multi-perspective image 70 is evaluated by means of a decoding unit of similar construction. A light box 71 illuminates the image 70 with the sub-images 70' and 70". A lens matrix 72 for a second group of radiation sources of the multiple radiation source produces a three-dimensional object image 73. The layer is imaged from a frosted pane 74 whose position can be shifted. The movement is realized by means of a sliding device 65. With the object 66, the layer is also imaged on the frosted screen 68 by the beam splitter 67. Both decoding arrangements decode identical layers from a single object, said layers being superposed to register on the frosted screen 68 in the described manner in order to form the complete layer image. The evaluation of the layer image is in this case realized, for example, by visual observation (75). Other layers of the objects are imaged by shifting or tilting of the frosted of the frosted panes 64 and 74 in synchronism with the shifting device 65.

Instead of layer imaging by optical means, electronic means (for example, TV) can also be used. Furthermore, the complete layer image 68 of FIG. 6, composed of the layer sub-images, can be displayed on a monitor. Similarly, the multi-perspective images 61 and 70 can be projected on transparent projection walls wherefrom they are decoded. The sub-image fields substitution of the various groups can then be projected simultaneously or successively in time. In the latter case, the layer sub-images produced by the decoding can be summed by means of a television storage tube in order to form the complete layer image.

FIG. 8 is a diagrammatic representation of a housing for the X-ray tubes used for irradiating the body to be examined. A large number of X-ray tubes are fixed in an oil filled container 100, (for example 24 dental X-ray tubes may be used). Each of the tubes is fixed on a socket 102 to enable easy replacement of the tube in the correct position and for the correct direction of radiation. Contact pins 103 are also provided in the container for control, high voltage and filament connections. A transformer 104 for pulse activation of the tubes is also located inside the container. It produces rectangular control pulses for the tubes. The container is normally filled with insulating oil. An aperture mechanism which is adapted to the exit windows of the sources may be provided underneath the bottom plate 105 (not shown). The tubes, are arranged inside the container so that all focal points are situated in one plane. In this case 24 separate images can be formed and registered in an optimum manner with respect to their auto-correlation for reconstruction and cross-correlation. The optimum positions of the tubes in this respect can be calculated in advance. One source maybe seperately in order to form a general picture of the patient for localization purposes.

What is claimed is:

1. Apparatus for examining objects comprising:
   a multiplicity of X-ray sources, each having a comparatively small X-ray focus;
   a first housing for a flat X-ray registration medium; and
   a second housing surrounding the X-ray sources, the X-ray sources being fixed within the second housing in a geometrical arrangement which permits mutually separable sub-images to be formed on the registration medium, the X-ray foci of all of the sources being situated in a single plane.

2. Apparatus as claimed in claim 1 in which the X-ray sources comprise fixed anode X-ray tubes which include filament-heated cathodes.

3. Apparatus as claimed in claim 2 further comprising transformer means, contained within the second housing, which function to produce high frequency pulses for activating the X-ray tubes.

4. Apparatus as claimed in any of the preceding claims wherein the second housing includes exit windows for transmitting X-ray beams generated by the X-ray sources and further comprising sockets which function to fix the positions of the sources within the second housing and which are rigidly coupled to the X-ray windows.

* * * * *